United States Patent
Bensimon et al.

(10) Patent No.: US 6,248,537 B1
(45) Date of Patent: Jun. 19, 2001

(54) USE OF THE COMBING PROCESS FOR THE IDENTIFICATION OF DNA ORIGINS OF REPLICATION

(75) Inventors: Aaron Bensimon, Antony; John Herrick; Olivier Hyrien, both of Paris, all of (FR)

(73) Assignees: Institut Pasteur; Centre Nationale de la Recherche Scientifique, both of (FR)

( * ) Notice: Subject to any disclaimer, the term of this patent is extended or adjusted under 35 U.S.C. 154(b) by 0 days.

(21) Appl. No.: 09/578,678

(22) Filed: May 26, 2000

Related U.S. Application Data

(60) Provisional application No. 60/136,792, filed on May 28, 1999.

(51) Int. Cl.⁷ ..................................... C12Q 1/68
(52) U.S. Cl. ................................. 435/6; 435/7.1
(58) Field of Search ........................... 435/6, 7.1

(56) References Cited

U.S. PATENT DOCUMENTS

| | | |
|---|---|---|
| 4,278,651 | 7/1981 | Hales . |
| 4,539,061 | 9/1985 | Saqiv . |
| 4,562,157 | 12/1985 | Lowe et al. . |
| 4,698,302 | 10/1987 | Whitehead et al. . |
| 4,724,207 | 2/1988 | Hou et al. . |
| 4,921,809 | 5/1990 | Schiff et al. . |
| 5,019,416 | 5/1991 | Honzawa . |
| 5,079,169 | 1/1992 | Chu et al. . |
| 5,098,977 | 3/1992 | Frautschi et al. . |
| 5,102,798 | 4/1992 | Guiseppi-Elie . |
| 5,178,947 | 1/1993 | Charmont et al. . |
| 5,215,882 | 6/1993 | Bah et al. . |
| 5,232,829 | 8/1993 | Longiaru et al. . |
| 5,237,016 | 8/1993 | Ghosh et al. . |
| 5,240,846 | 8/1993 | Collins et al. . |
| 5,330,891 | 7/1994 | Sutton . |
| 5,372,930 | 12/1994 | Colton et al. . |
| 5,447,841 | 9/1995 | Gray et al. . |
| 5,554,088 | 9/1996 | Zlojutro . |
| 5,610,287 | 3/1997 | Nikiforov et al. . |
| 5,624,711 | 4/1997 | Sundberg et al. . |
| 5,677,126 | 10/1997 | Bensimon et al. . |
| 5,840,862 | 11/1998 | Bensimon et al. . |
| 5,851,769 | 12/1998 | Gray et al. . |
| 5,866,328 | 2/1999 | Bensimon et al. . |

FOREIGN PATENT DOCUMENTS

| | | |
|---|---|---|
| 37 17 210 | 12/1988 | (DE) . |
| 0 125 995 | 11/1984 | (EP) . |
| 0 127 438 | 12/1984 | (EP) . |
| 0 350 407 | 1/1990 | (EP) . |
| 0 388 940 | 9/1990 | (EP) . |
| 0 391 674 | 10/1990 | (EP) . |
| 0 435 785 | 12/1990 | (EP) . |
| 0 578 148 | 1/1994 | (EP) . |
| WO 93/22463 | 11/1993 | (WO) . |
| WO 97/06278 | 2/1997 | (WO) . |

OTHER PUBLICATIONS

Bensimon et al., *Science,* vol. 265, pp. 2096–2098 (Sep. 30, 1994).
Keller et al., *PNAS,* vol. 86, pp. 5356–5360.
Schwartz et al., *Science,* vol. 262, No. 5130, pp. 110–114 (Oct. 1, 1993).
Parra et al., *Nature Genetics,* vol. 5, pp. 17–21 (Sep. 1993).
Zimmerman et al., *Nucleic Acids Research,* vol. 22, No. 3, pp. 492–497 (Feb. 11, 1994).
Lund et al., "Assessment of Methods for Covalent Binding of Nucleic Acids to Magnetic Beads, Dynabeads™, and the Characteristics of the Bound Nucleic Acids in Hybridization Reaction," *Nucleic Acids Res.* vol. 16, pp. 10861–10890 (1988).
Beattie et al., "Hybridization of DNA Targets . . . ", *Biotechnology,* vol. 4, pp. 213–255 (1995).
Netzer et al., "A New Approach to Construction . . . ", *J. Amer. Chem. Soc.,* 105(3), pp. 674–676 (1983).
Herrick et al., *Proc. Nat'l. Acad. Sci. USA,* 97(1), pp. 222–227 (Jan. 2000).
Herrick et al., *J. Mol. Biol.,* 300(5), pp. 1133–1142 (Jul. 2000).
Michalet et al., *Science,* 277(5331), pp. 1518–1523 (Sep. 1997).

Primary Examiner—James Ketter
(74) *Attorney, Agent, or Firm*—Finnegan, Henderson, Farabow, Garrett & Dunner, L.L.P.

(57) ABSTRACT

Eukaryotic genomes are duplicated by the activation of multiple bidirectional origins of replication. The replication programs of these cells depend on the temporal and spatial organization of replication origins throughout the genome. To investigate the replication program in a higher eukaryote, we employed a technique called molecular combing. This technique allows for a quantitative analysis of DNA replication on a genome wide basis. As a model system, *Xenopus laevis* sperm chromatin were differentially labeled at successive time points after the beginning of DNA synthesis. Genomic DNA was then extracted and combed on a glass surface. Direct measurements made on the labeled DNA provided a comprehensive analysis of the spatial and temporal organization of the *X. laevis* early embryo replication program and revealed that the number of replication origins activated per kilobase increases throughout the period of DNA synthesis.
local freq is 1/14 kb global is an increase of 5 fold per 100 kb each time point

28 Claims, 9 Drawing Sheets

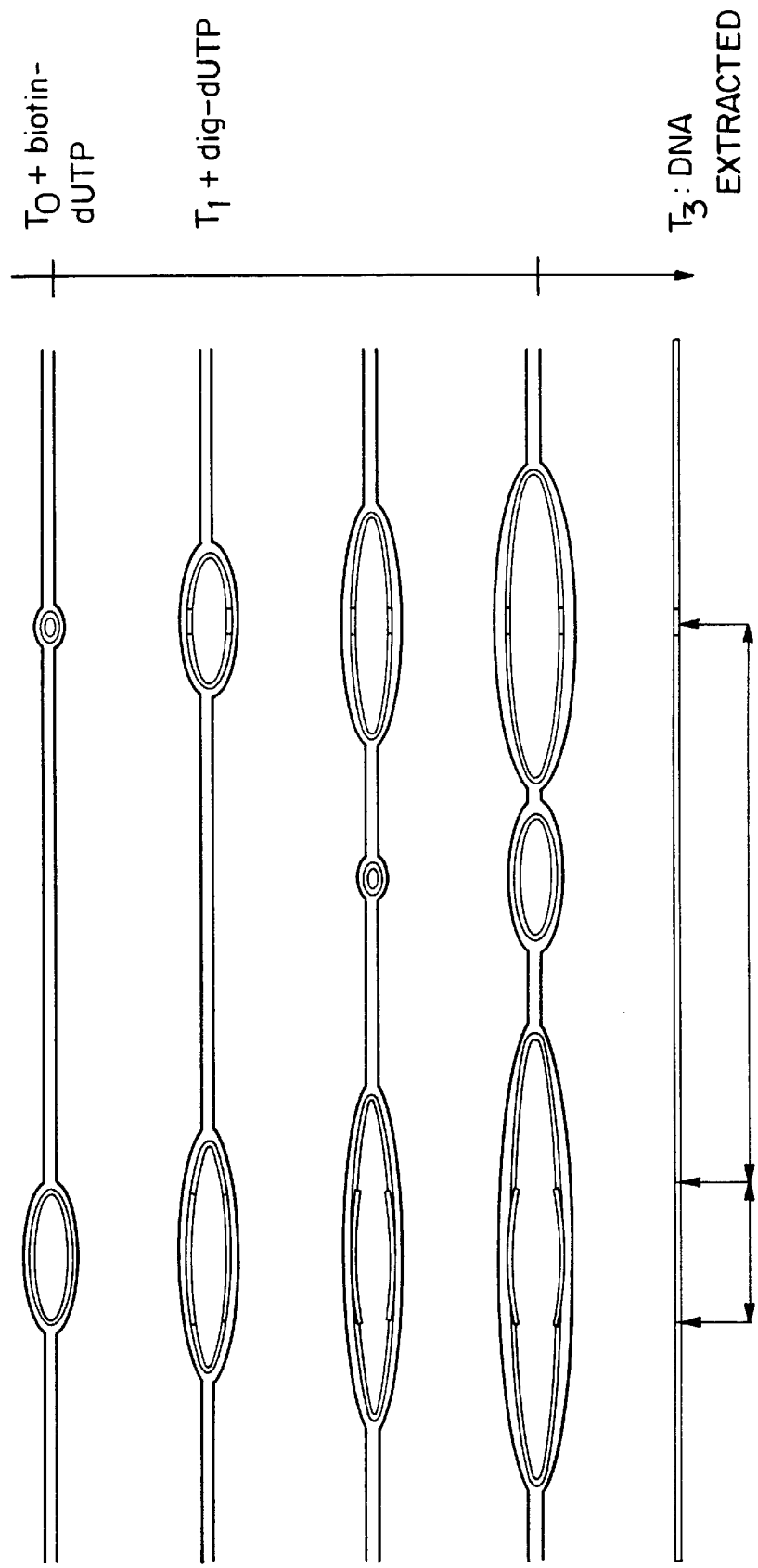
FIG. IA

USE OF THE COMBING PROCESS FOR THE IDENTIFICATION OF DNA ORIGINS OF REPLICATION

CROSS-REFERENCE TO RELATED APPLICATIONS

This application hereby claims the benefit under 35 U.S.C. § 119 (e) of U.S. provisional applications Ser. No. 60/136,792, filed May 28, 1999, the entire disclosure of which is relied upon and incorporated by reference herein.

BACKGROUND OF THE INVENTION

The present invention relates to methods of analyzing DNA replication, and more particularly to the use of molecular combing to facilitate the detection and identification (i.e., mapping) of origins of replication and the measurement of the dynamic and structural relationships regulating DNA replication.

Control of DNA synthesis is essential for maintaining genome stability (1, 2, 3). In higher eukaryotes, genomic instability associated with a loss of replication control and aberrant DNA synthesis is a key feature of a variety of neoplasms and genetic diseases (4, 5, 28). In yeast, an altered pattern of DNA synthesis leads to genomic abnormalities including aneuploidies and translocations (6, 7). The efficient and accurate replication of the genome in eukaryotes is accomplished by the activation of multiple bidirectional origins of replication. The temporal and spatial pattern of activation, or replication program, varies according to the developmental stage (8). In *X. laevis*, for example, the duration of the period of DNA replication during the cell cycle depends upon replicon size, or the distribution of replication origins (9). However, the organization and distribution of replication origins throughout the eukaryotic genome is not well known, and consequently the regulation of the replication program in these cells is poorly understood (10). This is primarily due to a variety of technical and fundamental obstacles which make it difficult to study DNA replication at the genomic level (11). Though a number of techniques exist for studying DNA replication in both higher and lower eukaryotes, more rapid methods are needed for the quantitative analysis of the dynamics of genome duplication (11).

SUMMARY OF THE INVENTION

To address the question of the spatial and temporal organization of DNA replication in a genome, we have employed the molecular combing method (12, 13, 14). The method of molecular combing is described in U.S. Pat. No. 5,840,862 (Bensimon et al.), which is incorporated herein by reference. Molecular combing permits high resolution physical mapping of specific genetic loci. The technique consists of uniformly aligning and extending genomic DNA on a substrate, such as a glass coverslip. The advantage of this method is that all molecules are aligned in one direction and identically stretched. The result is an exact correlation between the measured length of the stretched molecule and its size in kilobases. Consequently, this highly reproducible and precise method provides a unique opportunity to investigate how DNA replication is coordinated with other cell-cycle events.

This invention provides methods for localizing or identifying an origin of replication in a DNA molecule. In this method, replication intermediates corresponding to sequences of DNA in any and all regions of the genome (or on episomal/extrachromosomal replicating units, e.g. plasmids, viruses, double minute chromosomes, etc.) undergoing DNA synthesis are labeled with labeled nucleotides in vivo or in vitro. In vivo, the DNA is labeled by incorporation of the labeled nucleotide during DNA synthesis at all stages of the cell cycle. In vitro, the replication intermediates are labeled using cell free extracts of any organism including extracts from HeLa cells, *Xenopus laevis* embryonic cells (egg cell extract), *Saccharomyces cerevisiae, S. pombe, Eschericia coli*, etc., to incorporate the labeled nucleotides into the replicating DNA.

The genome can be differentially labeled to identify earlier and later replicating regions by labeling the entire genome continuously with one labeled nucleotide followed by a chase using a second labeled nucleotide at later stages of replication.

Appropriately labeled DNA is then combed on a surface for in situ analysis. More specifically, after DNA replication has terminated (one effective round of genome or DNA duplication), the DNA is extracted according to established methods. The purified DNA is then placed in a buffer, such as MES buffer, at the desired pH for combing, which is generally between a pH of 5 and 8, more particularly between a pH of 5 and 6, and most preferably at a pH of about 5.5. The sample DNA is then stretched and aligned by molecular combing on a surface, such as glass. Cosmid or PCR probes are then hybridized to the combed and labeled DNA using protocols developed in the lab in order to identify a specific region of the genome. This is necessary in order to map, or localize, the replication intermediates to any given region of the genome. The hybridized DNA is then washed and prepared for detection.

Labeled DNA and hybridized probes can be detected using appropriate antibodies (specific to the differentially labeled nucleotides) conjugated to a label, such as a fluorophore, in order to permit direct visualization of the labeled and hybridized DNA in an epifluoresence microscope. The surface containing the signals are washed to remove background and non-specific detection by the antibodies. The surface is then mounted in an appropriate buffer and examined. The detected signals (replication intermediates and hybridized probes) appear as linear fluorescent signals. Images of the signals are acquired and analyzed using software developed in the lab (CartographiX,© Institut Pasteur 1995; 1997 and CI tool,©: Institut Pasteur 1999) to permit high resolution mapping.

Replication origin locations can be mapped by comparing the location of the labeled replication intermediates with respect to the hybridized probes. More specifically, measurements are made on the sizes of the flourescent replication intermediate signals and their distances from the hybridized probes in the region. Origins are identified by monitoring the bidirectional evolution of the labeled replication intermediates from a kinetics experiment involving a chase at several different successive stages of replication. Origins are located at the centerpoints of the fluorescent signals (mapping resolution is approximately 1 to 4 kb), followed by cloning of the corresponding sequence using an established physical map of the region. The cloned sequences are tested for their ability to confer autonomous replication on episomal elements (e.g., plasmids). The corresponding nucleotide sequences are then analyzed by standard bioinformatic sequence analysis programs to identify sequence motifs. In addition, a CI tool can be used to establish spatio-temporal organization of origin of replication activities during the cell cycle (CI tool©, Institut Pasteur, 1999).

In particular, the methods of the present invention for mapping an origin of replication in a DNA molecule include the steps of:

a) incubating DNA undergoing replication in the presence of labeled nucleotides, which are incorporated into the replicating DNA;

b) aligning the DNA from step a) on a substrate;

c) hybridizing the aligned DNA with a nucleotide probe; and d) measuring the distances between the labeled nucleotides that were incorporated into the DNA during replication and the nucleotide probe to determine the location of the origin of replication with respect to the nucleotide probe.

The present invention also relates to methods of detecting an origin of replication in a DNA molecule, which include the steps of:

a) incubating DNA undergoing replication in the presence of labeled nucleotides, which are incorporated into the replicating DNA;

b) aligning the DNA from step a) on a substrate; and c) detecting the labeled nucleotides that were incorporated into the DNA during replication, where the labeled nucleotides are located in a region that corresponds to the origin of replication.

Another aspect of the invention relates to measuring the dynamic and structural relationships that regulate DNA replication. In particular, this aspect of the invention involves a method of measuring the rate of DNA replication, which includes the steps of:

a) adding a first labeled nucleotide to a reaction mixture of replicating DNA, where the first labeled nucleotide is incorporated into the replicating DNA;

b) adding a second labeled nucleotide to the reaction mixture at different time intervals following the addition of the first labeled nucleotide, where the second labeled nucleotide is incorporated into the replicating DNA;

c) aligning the DNA from the reaction mixture on a substrate;

d) detecting the first and second labeled nucleotides, which were incorporated into the DNA during replication; and e) measuring the distribution of the first and second labeled nucleotides in the aligned DNA to determine the rate of DNA replication.

To practice the methods of this invention, the labeled nucleotides can be detected with a labeled probe, such as an antibody conjugated to a label, where the probe recognizes and binds to the label in the labeled nucleotide. Examples of labeled nucleotides that are useful in practicing this invention include biotin-dUTP and digoxigenin-dUTP ("dig-dUTP"). The term "labeled nucleotides" also includes modified nucleotides, such as bromodeoxyuridine, chlorodeoxyuridine, iododeoxyuridine, etc. The DNA can be incubated with the labeled probes before or after the DNA is aligned on the substrate by the process of molecular combing. The DNA can also be washed prior to being aligned on the substrate or following incubation with the labeled probe in order to eliminate non specific reagents, such as unbound labeled probe or unincorporated labeled nucleotides.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with description, serve to explain the principles of the invention.

BRIEF DESCRIPTION OF THE DRAWINGS

FIG. 1A represents the experimental scheme of the present invention. Xenopus sperm nuclei were incubated in the presence of biotin-dUTP at t=2' in order to label the entire genome. At different time points following the beginning of S-phase, dig-dUTP is added in addition to the biotin-dUTP to differentially label the later replicating DNA sequences. Earlier replicating sequences (those that have replicated before the addition of dig-dUTP) will appear as red linear signals while later replicating sequences (those that replicate after the addition of dig-dUTP) will incorporate dig-dUTP and biotin-dUTP simultaneously and consequently will appear as yellow linear fluorescence signals (merge green+red). The DNA is then allowed to complete replication (120 min following addition of the extract) and the nuclei are harvested. Genomic DNA is then extracted and combed on glass cover slips. The combed DNA is detected using antibodies conjugated either with red (e.g., Texas Red) or green (e.g., FITC) fluorophores. The labeled DNA is observed in an epifluorescence microscope (Axioskop, Zeiss, Plan Neofluar 100X objective) with an attached cold CCD camera. Measurements are then performed on each individual molecule present in a series of randomly selected fields of view. Individual measurements were made on both earlier and later replicating sequences (red for earlier replicating sequences, and yellow for later replicating). Measurements were likewise made on the sequences between the mid points of the adjacent red labeled segments. Together, these measurements provide an assessment of replication unit sizes and replicated sizes from randomly selected regions of the genome. Each sample contained approximately 20,000 haploid genomes, and over 10 Mb of DNA were analyzed for each time point.

DETAILED DESCRIPTION

Figure 1B:
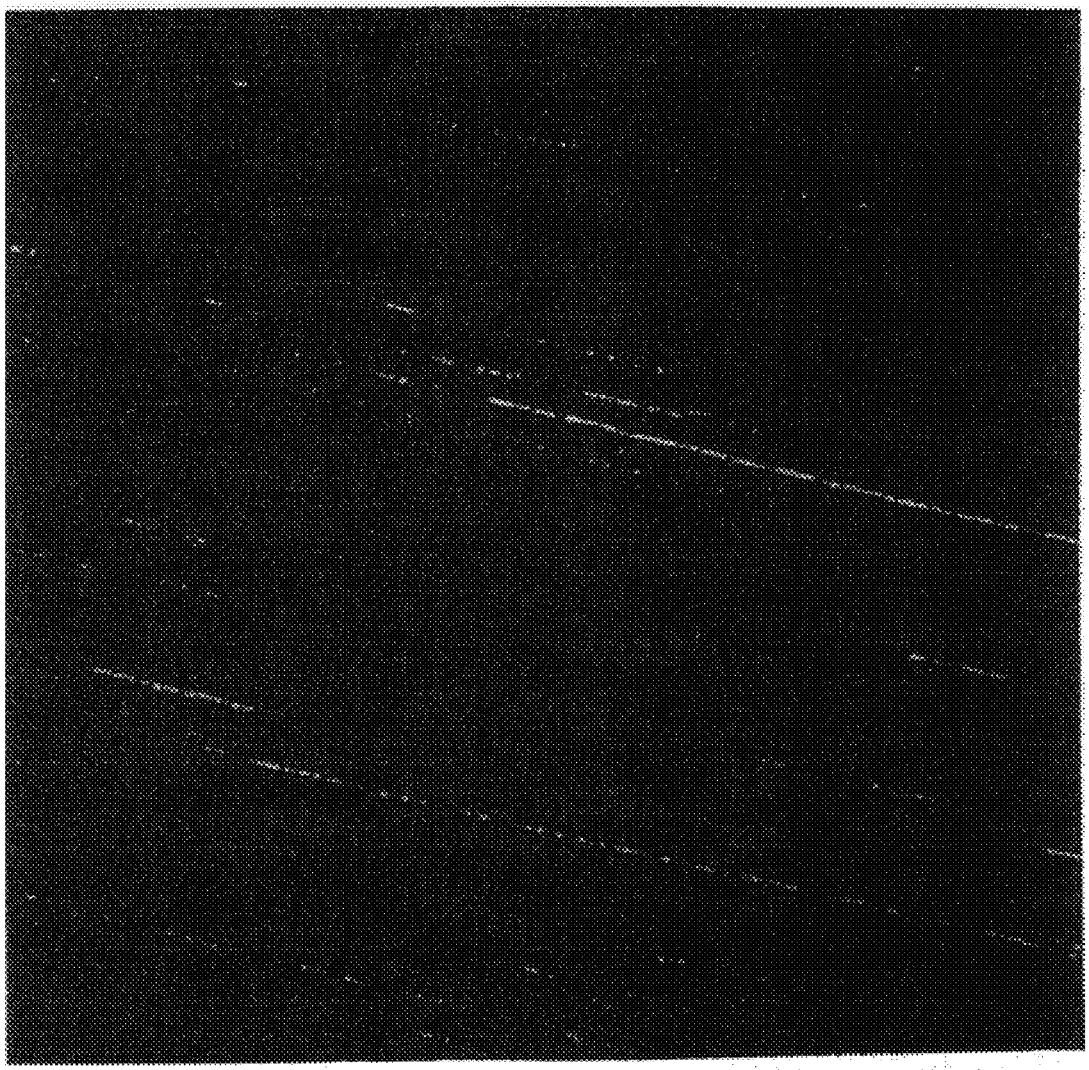
FIG. 1B is a photograph of combed DNA visualized using FITC- and Texas Red-conjugated antibodies. Sequences stained in red correspond either to replication bubbles or to molecules that have finished replication prior to the addition of dig-dUTP.

The in vitro DNA replication system of *Xenopus laevis* was chosen as a model to investigate the full potential of molecular combing for studying DNA replication. This system uses egg extracts to replicate exogenous DNA and supports one complete round of replication (15, 16). In this experimental system, *Xenopus laevis* sperm chromatin was labeled with biotin-dUTP and dig-dUTP. Biotin-dUTP was added immediately after the extract (t=2') in order to label the entire genome. At different time points (i.e., t=25, 29, 32, 39, and 45 min) following the addition of the extract, dig-dUTP was added in order to differentially label the later replicating DNA (16). Genomic DNA was then extracted and combed on the glass surface.

More specifically, in the experimental system used here, approximately 20,000 nuclei were continuously labeled using 20 μL of egg extract in the presence of 20 μM of biotin-dUTP. DNA synthesis began within 15 minutes after the extract was added to the sperm chromatin and 90% of the nuclei terminated DNA synthesis 45 minutes later (data not shown). At successive time points following addition of the extract, 50 μM of dig-dUTP was added, yielding a series of five samples with differentially labeled DNA. Each sample was then prepared according to standard protocols, stained with YOYO-1 (a dimeric cyanine dye that fluoresces upon binding to nucleic acids) and combed on a substrate, such as glass (13).

The combed DNA was examined in an epifluorescence microscope to determine the average number and size of the molecules combed per field of view (FOV). In this case, the average number of molecules per FOV was 20 and the average size of the molecules was 200 kb. This corresponds to approximately 30 haploid genomes combed per 22 mm×22 mm coverslip.

Earlier and later replicating regions of the genome were then detected using antibodies conjugated different fluorochromes. For example, Texas Red-conjugated antibodies were used to detect the biotin-dUTP labeled earlier replicating sequences, while FITC-conjugated antibodies were used to detect the later replicating dig-dUTP labeled sequences. It should be noted that the later replicating sequences are labeled with both biotin-dUTP and dig-dUTP.

All five samples were then analyzed in an epifluorescence microscope. Images of the combed molecules were obtained using a CCD camera. Measurements were then made on individual molecules using software developed in the lab. Approximately 10 Mb from each sample was measured in this manner, and the respective lengths of the alternating red and green segments were precisely determined and their distributions analyzed as histograms.

No significant bias with respect to the incorporation of labeled nucleotide was observed. Incorporation was 84.41% for biotin-dUTP and dig-dUTP incorporation was 84.93%. The replication fork velocity was found to be the same in either the presence or absence of biotin-dUTP. As a control, one sample was continuously labeled with both biotin-dUTP and dig-dUTP so that the entire genome could be visualized using either the red or green fluorescence filters. Measurements made on this sample were used to determine the efficiency of nucleotide incorporation and detection.

In this manner, replication units were visualized using red fluorescing antibodies (e.g., Texas Red), while those regions that replicated after the different time points (i.e., after the addition of dig-dUTP) are double labeled and so were visualized using both green (e.g., FITC) and red fluorescing antibodies (FIG. 1B). This approach permits direct mapping and quantitative analysis of the alternating red and green replication units along each individual DNA molecule.

One of the principal difficulties in studying DNA replication in metazoan genomes is the apparent lack of well defined origins of replication (17, 18). In these cell systems apparently any DNA sequence can be replicated provided it is large enough (17, 18). This suggests that initiation of DNA replication is random with respect to sequence. This sequence independent activation of DNA synthesis raises the question of whether or not DNA is replicated according to a stochastic process (19, 20) or according to a mechanism that imposes a regular temporal and spatial organization on the replicating chromatin (21). Since origins must be closely spaced in order to complete DNA replication in pace with the cell cycle, a mechanism was proposed according to which periodic chromatin folding ensures the regular spacing and activation of replication origins throughout the genome, an organization that thus guarantees the complete duplication of the genome before entry into mitosis (21).

To investigate the spatial distribution of the red and green stained replication units, images of the aligned labeled molecules were acquired and measurements were systematically performed on the labeled DNA for each time point (FIG. 1B). Measurements were performed on all molecules in each randomly selected field of view for each time point, and a total sample length of over 77 Mb was analyzed. Therefore, these measurements provide a statistical assessment of the distributions of replication unit sizes as well as the distances between them. Eye size is the term used here to refer to the earlier red stained replication units; while inter-eye size is the term used to refer to the later green and red stained replication units.

Eye-to-eye distance is likewise defined as the distance (in kb) between the midpoints of two adjacent eyes (FIG. 1A). The extent to which each individual molecule has undergone replication prior to the addition of the second labeled nucleotide was determined as the sum of the lengths of the replication eyes (red) divided by the total length of the measured linear molecule. In this manner, eye to eye distances and eye sizes can be analyzed in terms of the extent to which the molecules have undergone replication. This is necessary since the genomes of the nuclei begin replicating asynchronously over the population.

Figure 2A:
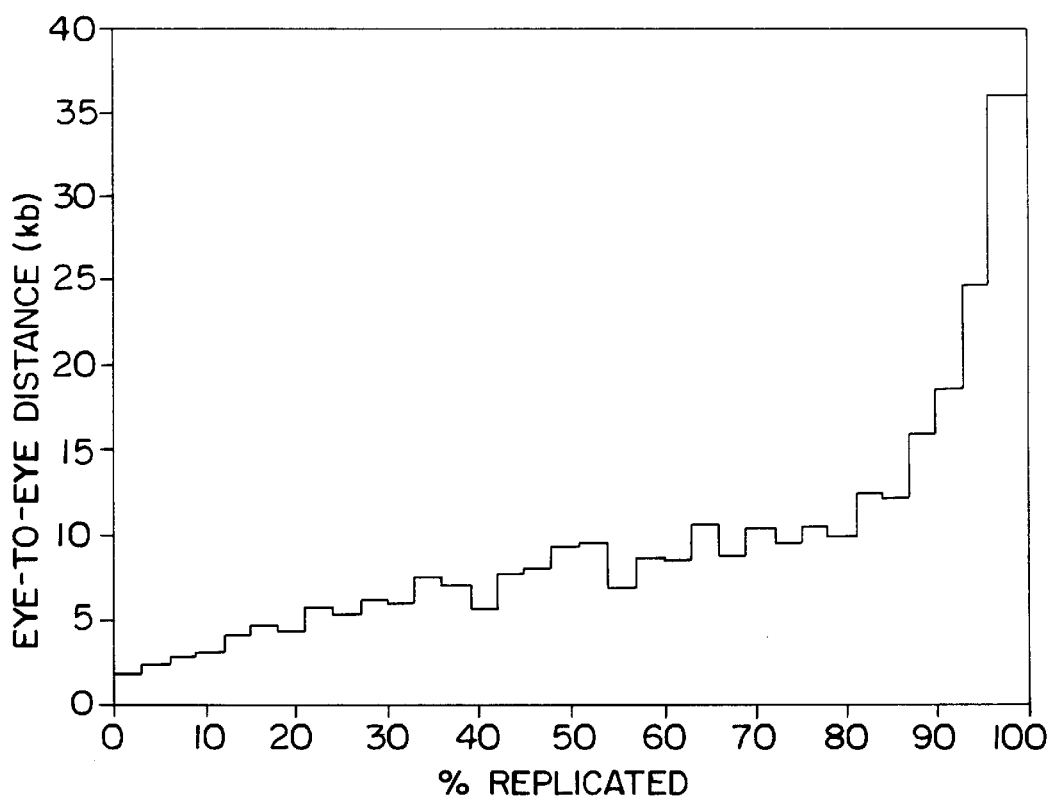
FIG. 2A is a graph representing the eye to eye distance versus the percentage replicated. Measurements were made on a population of individual molecules from each time point. Replication eye sizes were measured as linear red signals. The extent to which each molecule had undergone replication (percent replicated) was determined by summing the eye sizes for each molecule and then dividing by the molecules total length (see scheme). Molecules were then analyzed as histograms according to eye size versus percent replication. This was done individually for each time point (data not shown) and for the entire sample (all time points). The replication fork velocity was estimated by measuring the rate at which the linear red signals (replication eyes) increased in size during the S-phase. This is done by determining the increase in the slope of the curve for molecules that are between 0 and 80% replicated. In this manner, the replication fork velocity was found to be 300 bp/min. This is a lower estimate of fork velocity since it is an average over the entire population of molecules. It is not possible to directly measure the increase in eye size due to the fact that DNA synthesis begins asynchronously over the population of nuclei.

The measurements revealed that eye sizes increase linearly until 87% of the sample has been replicated at which point eyes rapidly increase in size due to the merging of adjacent replication forks (FIG. 2A). According to the data presented in FIG. 2, the replication fork velocity was estimated from the mean increase in eye size and was found to be about 300 bp/min. This value is consistent with previously reported values (9, 22). However, it is a lower estimate of fork velocity since the replication asynchrony of the population of nuclei will result in a slower than expected increase in the observed eye sizes. This asynchrony has been reported to lead to an overestimation of 10 to 20 minutes in the length of S-phase (9, 23). If the period during which DNA synthesis occurs over the population corresponds to 20–30 minutes, then for an individual genome the average S-phase will last approximately 10 to 15 minutes. Therefore, the actual replication fork velocity corresponds to approximately 600 bp/min. (22).

Figure 2B:
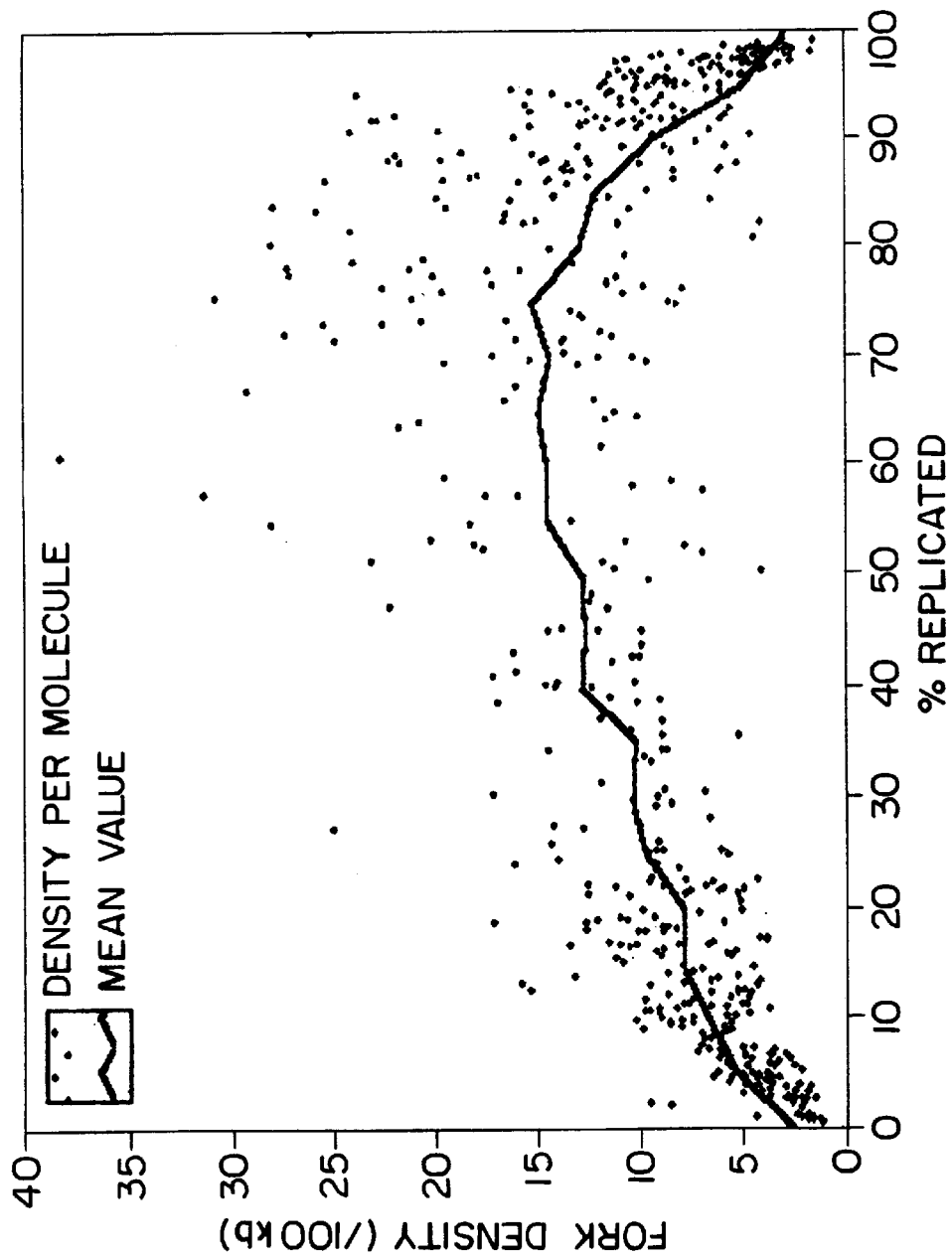
FIG. 2B is a graph representing the replication fork density versus the percentage replicated. Molecules were grouped in bins according to their stage of replication (% replicated) and the fork density was computed from the number of eyes per bin divided by the total length of all molecules in each bin. This, in turn, yields the number of replication forks, which is simply twice the number of replication eyes (for bidirectional replication). Mean replication fork density increases over 3 fold when the DNA is between 6% and 60% replicated and rapidly decreases after more than 87% of the molecules have been replicated.

We next looked at the replication fork density, which is simply twice the number of eyes/kb, and we observed that the fork density increases over three fold during the first half of the period of DNA synthesis (i.e., from 25 min. to 32 min.). The replication fork density then rapidly decreases as eyes begin to merge (FIG. 2B). Although this suggests that replication is initiated primarily during the first half of the S-phase, measurements made on the later replicating samples also revealed that some residual initiation still occurs even after 96% of the DNA in the sample has been replicated. Indeed, for molecules that are over 90% replicated, up to 28% of the replication eyes are between 3 and 8 kb. Assuming that these forks emanate from a single initiation event, this observation indicates that a significant number of initiation events occur late in S-phase (Table 2).

Figure 3A:
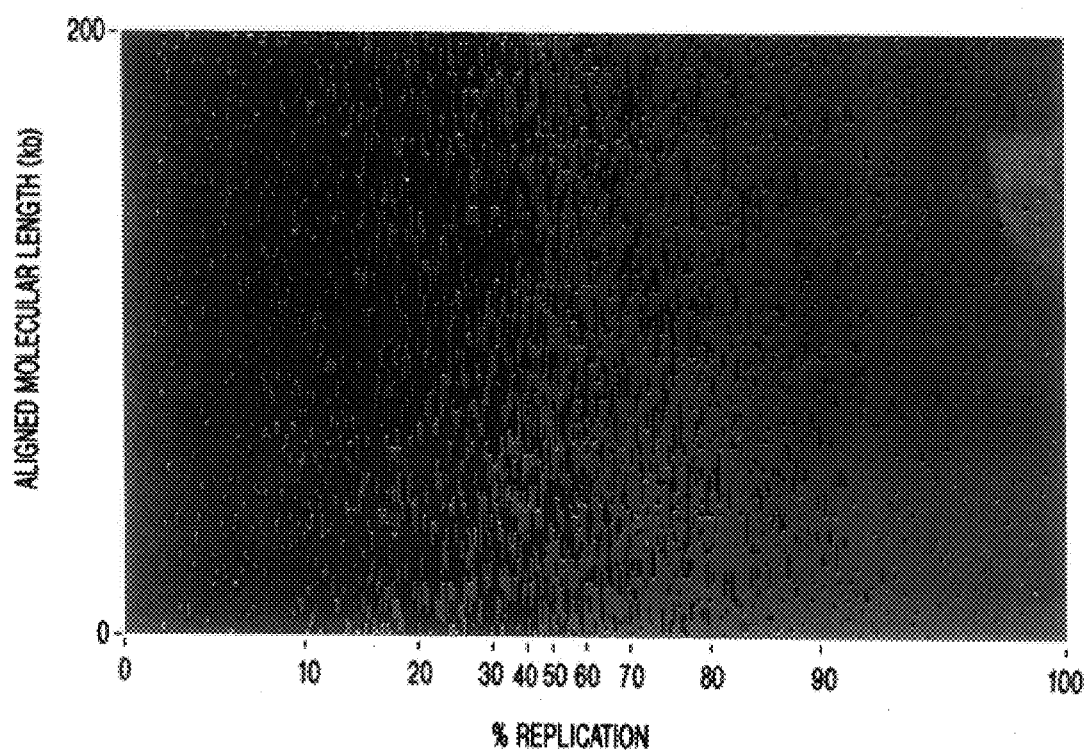
FIG. 3A is a computer generated reconstruction of all molecules measured during the experiment. Molecules were reconstructed directly from the measurements made on the combed DNA. The reconstructed molecules were then selected at random and aligned end to end according to their respective stages of replication. Replication eyes, or earlier replicating sequences, are visualized in red while later replicating sequences are visualized in green. A total of 77 Mb of DNA were measured during the experiment and aligned in 200 kb columns according to their percent replication. In this manner it is possible to directly visualize the different stages of replication that the DNA has undergone, with each stage corresponding to a given percent replication.
Figure 3B:
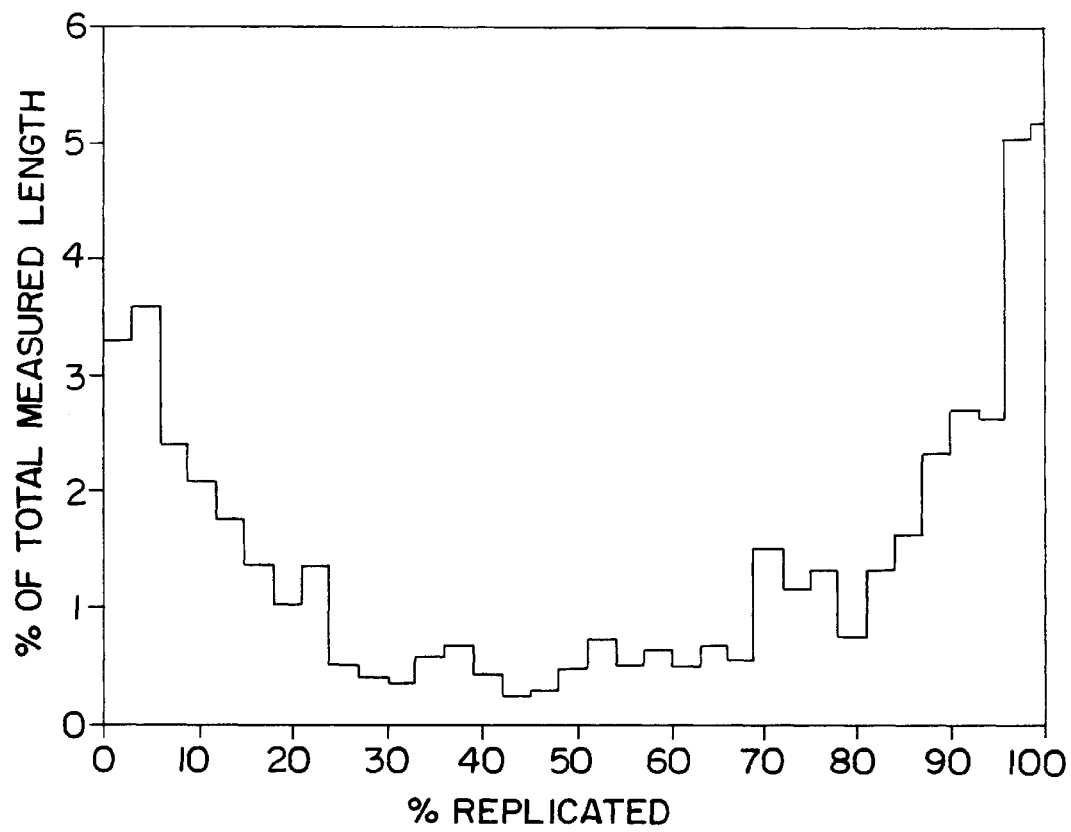
FIG. 3B represents the fraction of total measured length (77 Mb) versus the percentage replicated. Molecules were grouped according to the percent replication they had undergone and their lengths summed in order to determine the respective percentage of the total length that they represent. This yields the distribution of the total length measured during the experiment in terms of percent replication, which is visually represented in FIG. 2A. Note that the smallest fraction of the sample occurs when the molecules are between 40% and 50% replicated. This indicates that the maximal rate of DNA synthesis occurs when 40% to 50% of the DNA has been synthesized.

FIG. 3 is a computer reconstruction of all molecules measured during the experiment. It shows the evolution of the replication program as DNA synthesis advances. This can be quantified as a histogram showing the fraction (in terms of length) of the total sample at a given stage of replication (FIG. 3B).

According to FIGS. 2B and 3B, the rate of DNA replication depends on the replication fork density at any given stage of replication. The forks correlate with origins, and how origins are spaced is an important parameter in determining the duration of S phase. Therefore, it is useful to determine the distances between the midpoints of neighboring earlier replicating segments since these measurements provide information about the spatial distribution of replication origins (24).

Figure 4:
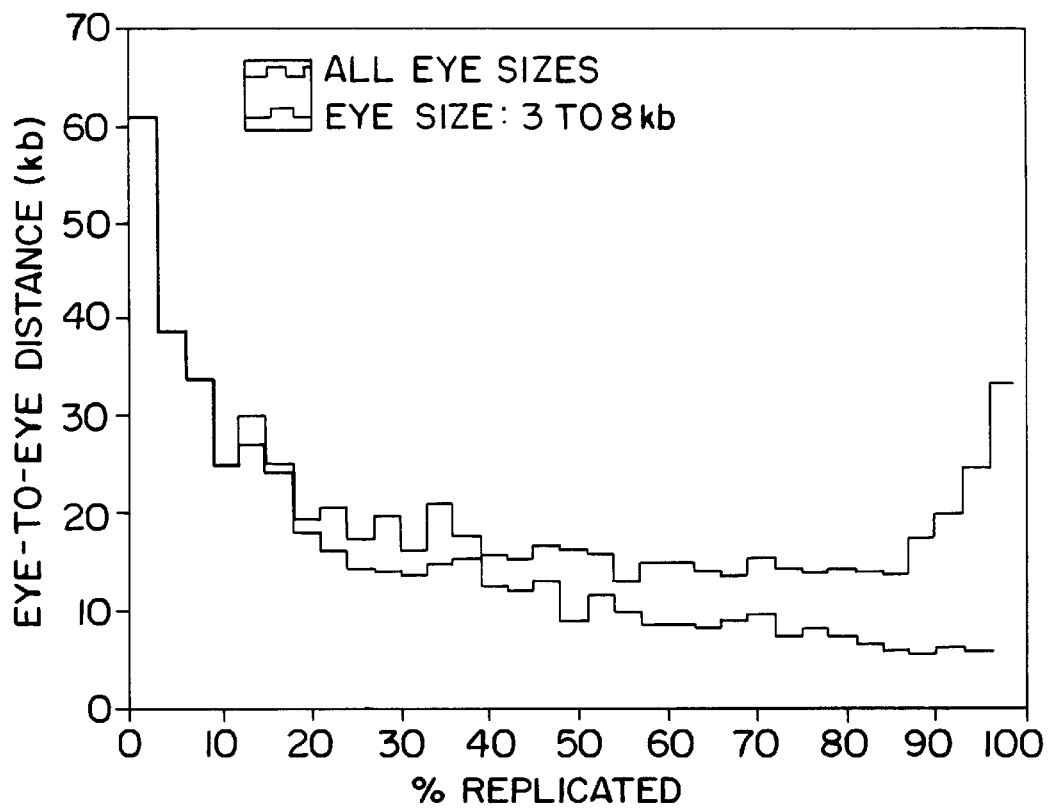
FIG. 4 is a graph representing the mean eye to eye distance versus the percentage replicated. The distances between the midpoints of adjacent replication eyes were measured. Measurements were made on individual molecules in each sample and analyzed in terms of the extent they had undergone replication. Eye to eye distances versus the percent of DNA replicated per molecule provides an assessment of how replication origins are distributed and activated during S-phase. According to the histogram, a plateau occurs between 37% to 87% replication. This plateau corresponds to an average eye to eye size of 14 to 16 Kbp throughout the genome during S phase. Therefore the average replicon size in the *X. laevis* genome at this stage of development can be estimated to be approximately 15 kb. The red curve shows the evolution of eye to eye distances assuming that eye sizes between 3 and 8 kb correspond to forks emanating from a single initiation event. Eye to eye distances between eyes in this size range indicate that initiations occur with a minimum average spacing of approximately 6 kb.

Eye to eye distances were measured and separately plotted against the extent to which the respective molecules had already undergone replication (see above). The correlation between the mean eye to eye distance and the extent of DNA replication reveals a plateau at an average of 14 to 16 kbp (FIG. 4). The plateau occurs when the DNA has undergone between 37% and 87% replication. This corresponds to the interval between 32 and 39 minutes, respectively, and indicates that most of the DNA is being replicated within a narrow window of approximately 10 minutes. This is in contrast to the observed 20 to 30 minute period during which the DNA is synthesized and is consistent with previous assessments of the length of S-phase at this stage of development (see above; FIG. 4). It should be noted that the rapid increase in eye to eye distances occurring at 87% replication is consistent with the same value observed for the rapid increase in eye sizes mentioned above. This demonstrates the accuracy of molecular combing since eye sizes and eye to eye distances represent two independent measurements of the same biological phenomenon.

We next examined changes in mean eye to eye distances for each sample and observed that the average distance decreases rapidly from 25 to 32 min and then increases as replication eyes expand and adjacent forks begin to merge. These results are summarized in Table 1.

TABLE 1

| Time (min) | Fraction Replicated (%) | Eye Size (kb) | Inter-Eye Size (kb) | Eye-to-Eye Size (kb) | Fork Density (/100 kb) |
|---|---|---|---|---|---|
| 25 | 5.14 ± 3.7 | 2.5 ± 1 | 29.7 ± 21.3 | 32.2 ± 21.2 | 4.9 ± 2.3 |
| 29 | 17.79 ± 14.1 | 5.4 ± 4.7 | 18.8 ± 17.3 | 24.9 ± 17.7 | 7.9 ± 4.1 |
| 32 | 47.27 ± 24.6 | 8.9 ± 8.8 | 8.7 ± 9.6 | 17.7 ± 11.5 | 11.9 ± 4.7 |
| 39 | 89.49 ± 10.9 | 13.5 ± 13.8 | 2.8 ± 3.3 | 16 ± 10.6 | 13.4 ± 6.7 |
| 45 | 96 ± 5.1 | 20.6 ± 22.3 | 2.5 ± 2.1 | 18.7 ± 10.3 | 8.4 ± 5.6 |

In Table 1, each sample corresponds to a given time point (i.e., t=25', 29', 32', 39', and 45') at which dig-dUTP was added to the replicating DNA. The differentially labeled DNA (biotin-dUTP and biotin-dUTP/dig-dUTP) was then allowed to complete replication (t=120'). Samples were individually prepared and combed on a coverslip. Measurements were then made on each individual sample. An average of 10 Mb was analyzed per sample, and the mean values for each sample parameter are presented in Table 1.

The second column represents the amount of DNA replication that occurred prior to the addition of the second nucleotide and was determined by measuring the red labeled segments in each molecule and then dividing that by the total length of the molecule. This was done for each molecule in the sample in order to ascertain the mean percent replication over the sample.

In column three, the mean eye size for each sample was obtained from direct measurements of eye size for each molecule analyzed. Because the DNA can shear during its preparation, labeled segments at the extremities of the molecules were not included in the assessment of mean eye size, inter-eye size or eye to eye distance.

In column four, inter-eye segments were measured as discussed above for mean eye size. These segments correspond to sequences replicated after the addition of the second nucleotide and, therefore, represent unreplicated sequences at the time the second nucleotide was added. In the fifth column, eye to eye sizes were computed as the distance between the midpoints of two adjacent eyes flanking one intervening inter-eye segment.

As represented in the last column, mean fork density was determined as twice the number of eyes per unit molecular length. As the number of new forks per unit length increases, eye to eye distances decrease, and the frequency of initiation exceeds the frequency of termination (fork mergers). The relative fork density increases approximately 1.5 times from time point to time point until t=39', at which point termination begins to dominate.

As indicated in Table 1, the mean eye to eye distance for each sample decreased up to three fold until the plateau was reached. This decrease is consistent with the three fold average increase in the replication fork density observed over each successive sample. Likewise, the average rate at which forks form per kb is consistent with the average rate at which eye to eye distances decrease. Indeed, the mean fork density over the plateau (between 40% and 80% replicated) corresponds to 15 forks per 100 kb (FIG. 2B). An average of 7 replication eyes (15 forks) every 100 kb would, therefore, yield an average eye to eye distance of approximately 15 kb, as observed (FIG. 4).

Our analyses of eye to eye distances reveal no regular pattern of replication during DNA synthesis, suggesting that the genome is indeed duplicated according to a random replication process (data not shown). In a random process, some replications will be too large to be completely replicated in a 10 to 15 minute time interval, if replication fork velocity is constant (19, 20). Therefore, we examined the sizes of later replicating sequences (inter-eye sizes) for each sample as a function of the extent to which the molecule had undergone replication.

Assuming that no new replication forks are formed, a molecule that is 70% replicated will normally require 3 minutes (S phase=10 minutes) to complete its duplication at a fork velocity of 600 bp/min. We found, however, that 72% of the molecules between 70% and 99% replicated contained inter-eye sequences whose sizes would require more time to replicate than is actually observed (data not shown). The fraction of the genome at the end of S phase that would remain unreplicated in the absence of new initiation events is shown in Table 2.

TABLE 2

| Time (min) | New Forks (%) | F S-Phase = 10 min (%) | F S-Phase = 16 min (%) | Max, exceeding replication time (min) |
|---|---|---|---|---|
| 25 | 98 | 99 | 98 | 120 |
| 29 | 76 | 98 | 91 | 79 |
| 32 | 61 | 85 | 75 | 51 |
| 39 | 43 | 22 | 14 | 21 |
| 45 | 28 | 12.5 | 8.7 | 17 |

In Table 2, new forks are defined as those forks corresponding to replication eyes that are between 3 and 8 kb in size. The fraction of new forks in each sample was computed as the percentage of new forks with respect to the total number of forks in the sample.

Columns three and four list the fraction (F) of the total sequence length in each sample containing inter-eye segments (unreplicated sequences at the time the second nucleotide was added) whose replication time would exceed the time remaining to replicate the respective molecule (shown in terms of % total length of the sample).

The last column lists the largest observed unreplicated sequence for each time point with respect to the amount of time its replication would exceed that of the corresponding molecule. Although most molecules between 70% and 99% replicated contain sequences that are too large to replicate in the 10 to 15 minute interval of S phase, only a certain number of these are considered to be significant. In most cases, these sequences require a replication time in excess of 30% to 40% of the length of S phase.

As discussed above, the fractions (F) listed in Table 2 correspond to inter-eye segments that require a replication time in excess of the time normally needed to replicate the respective molecule. For example, after an elapsed time of 10 min, about 12% of the total length of the sample having undergone 96% replication (t=45') would remain unreplicated in the absence of new initiations. Indeed, if only two forks were employed, the largest later replicating segment (for a molecule that was already 82% replicated) would have required a replication time that is 17 minutes longer than the observed duplication time of the genome. This observation along with the large standard deviations observed in eye sizes and eye to eye distances suggest that origins are randomly dispersed throughout the genome according to a stochastic process. It should be noted, however, that these observations do not exclude the possibility of a non-random higher level organization of DNA replication, and refer to segments of the genome that generally vary between approximately 10 and 300 kb in size (25).

The random size distribution of replication eyes and eye to eye sizes for each time point (data not shown) indicates that origins are activated during S-phase without any apparent temporal or spatial organization. Since any segment of the genome is replicated once and only once, the observation that new forks are formed throughout the entire S-phase suggests that the number of newly formed forks per kilobase may potentially be increasing as S-phase progresses (FIG. 2B; Table 2). The critical factor in this case is the fraction of DNA that remains to be replicated at the time the forks are formed. This fraction corresponds to the green stained or inter-eye segments of the molecule. Therefore, assuming that two new forks correspond to a single initiation event, it is necessary to calculate the number of initiation events that occur per non-replicated fraction of each molecule.

This is done by calculating back in time from the sizes of the replication eyes and then determining the fraction of DNA remaining to be replicated at that time. More specifically, the initiation frequency is calculated by sorting replication eyes according to their sizes and then determining the density of replication eyes that fall between 3 and 8 kb in size. This interval is an estimate of the number of eyes emanating from a single initiation event given that the mean replicon size is 14 to 16 kb. Initiation events for each molecule are then mapped in time by calculating back from the replication eye size: $t_1=L_{eye}/(2\times\text{fork velocity})$. The number of initiation events per molecule is then determined with respect to the fraction of the molecule that remains to be replicated at the time the events occurred. The number of events per non-replicated segment, here called the nucleation density, is then compared to the amount of DNA already replicated at that time for that particular molecule.

Figure 5A:
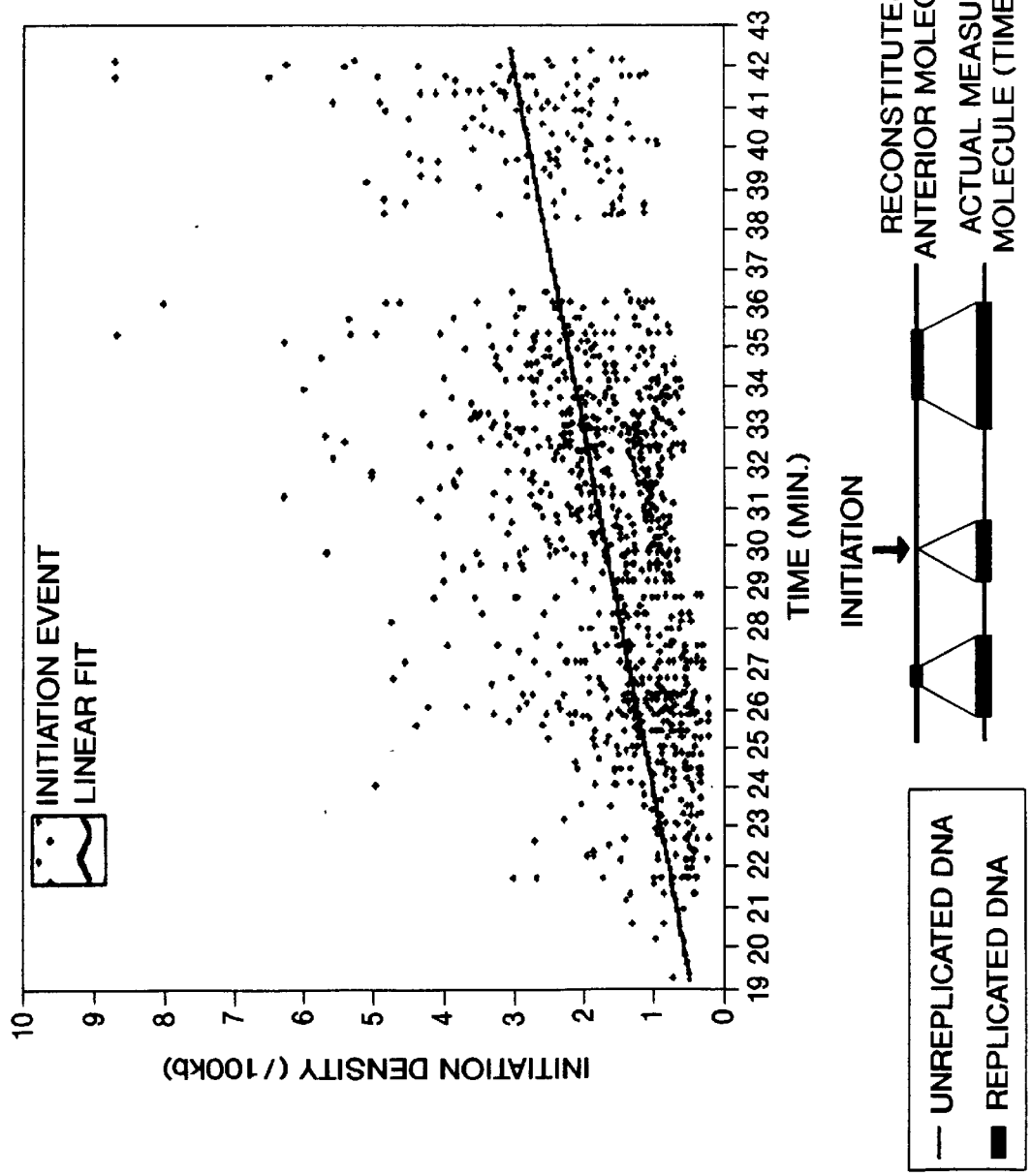
FIG. 5A is a graph representing the number of nucleation events (/100 kb) versus time. Nucleation events were defined as adjacent replication forks that are less than 8 kb apart. This upper value corresponds to one half the mean eye to eye distance (14 to 16 kb), and serves as an estimate of those forks most likely to have originated from a single initiation event. A lower limit of 3 kb was established by quantifying the background observed in a doubly substituted sample of combed genomic DNA (data not shown). These measurements agree with previous observations on the resolution of molecular combing, which is known to be 1 to 4 kb. From the eye size (red segments of the actual measured molecule) and the replication fork velocity, the time a given eye began replicating can be determined (arrow). The fraction of the molecule that remains to be replicated at the time of that nucleation event is next determined for each reconstituted molecule. This yields the relative fraction of unreplicated DNA per nucleation per molecule; and the inverse of this value in turn yields the nucleation density (event per kilobase). This was done for each molecule in a given sample and the corresponding nucleation density was plotted with respect to time. The red line shows the mean density over successive three minute intervals
Figure 5B:
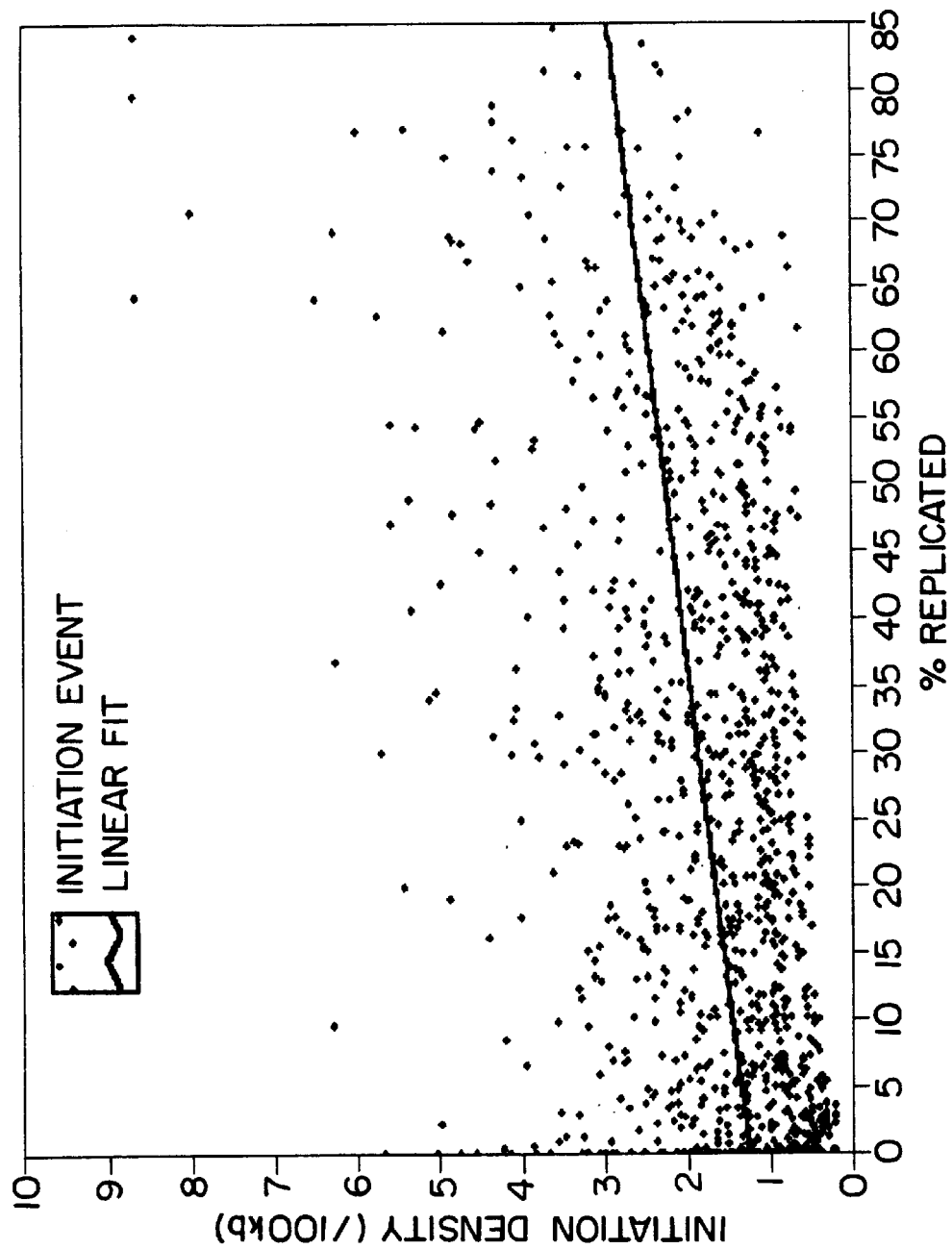
FIG. 5B is a graph representing the number of nucleation events versus the percentage replicated. Nucleation events were determined as described for FIG. 5A. The number of events per molecule was then plotted versus the percent each molecule had been replicated. The red line corresponds to the mean density with respect to percent replication.

In this manner, we found that the number of nucleation events per non-replicated fraction of the DNA increased both in time and with respect to the percentage of DNA already replicated in each sample (FIGS. 5A and 5B). The mean increase from the onset of replication to the termination of DNA synthesis was found to be at least 3.5 fold. In some instances, the increase was as much as 9 fold.

The frequency of initiation calculated using this approach yields a lower limit on the number of events per kilobase per minute. According to this method, all replication eyes smaller than 8 kb. are assumed to correspond to individual initiation events, whereas this is not the case if initiations occur according to a stochastic process. However, this bias does not significantly affect the measurement of the average increase in initiation frequency during S-phase.

Interestingly, it was observed that the later time points (i.e., t=39' and t=45') had an overall higher nucleation density at all stages of replication (Table 2). This observation indicates that, on average, replicon sizes of later replicating DNA regions are smaller than those of earlier replicating regions. The increase in the density of new forks leads to a corresponding reduction of eye to eye distances. An average eye to eye distance of 6 kb was observed for molecules that were between 80% and 95% replicated (FIG. 4). Assuming an S phase of 10 minutes and a fork velocity of 600 bp/min., these sequences are replicated in approximately 5 minutes. This observed acceleration in the rate of DNA synthesis can adequately account for the duplication of the genome without the need to invoke a mechanism that organizes the DNA into regularly spaced replication units.

The largest replication time in excess of S phase was 17 minutes for a molecule that was approximately 82% replicated. Assuming no new initiations, only two forks will replicate this segment, which is 38.4 kb at the beginning of S phase. For a molecule that is 82% replicated, at least 2.7 minutes are required to complete its replication, again assuming only two forks are present on the molecule. The size of the unreplicated segment at that stage is 23.6 kb. However, if the initiation frequency increases up to 4 fold, then 8 forks will form to replicate the segment (mean eye to eye size=6 kb). If two forks require 19.7 minutes, then with 8 forks the segment will be replicated in approximately 4.9 minutes (23.6 kb/(8×600 bp per minute). This is reasonably consistent with the time required to replicate the molecule itself (i.e., 2.7 minutes) during an S-phase that lasts 15 minutes. Indeed, a 7 fold increase in frequency would result in the segment's replication in as little as 2.8 minutes.

The present results extend our understanding of the mechanisms of DNA replication, particularly in eukaryotes and more particularly in *Xenopus laevis* early embryos. These data confirm previously reported results concerning the dynamics of S-phase and the spatial organization of replicons in the *X. laevis* early embryo. A random spatial organization of replications has been reported for the rDNA region at this stage of development (27). Our results extend this observation to the genome itself and indicate that origins of replication are dispersed throughout the genome at irregular intervals but with an average interval of 15 kb. Given that the replication fork velocity is 600 bp/min., the average length of the S-phase will be approximately 12.5 minutes. This short S-phase would suggest that the replication program is controlled by a nonrandom mechanism that imposes a regular spacing between replication origins (21).

However, a significant fraction of the molecules analyzed here contain unreplicated sequences in excess of what would be expected for a 10 to 15 minute S phase. This indicates that even at later stages of replication, a significant number of origins are too widely dispersed for the intervening sequences to be replicated in the allotted time interval. However, our observation that nucleation density increases as S phase progresses suggests that the relative rate of DNA synthesis accelerates toward the end of S phase. This observation may account for how an apparently random replication program can successfully duplicate the entire genome before the onset of mitosis.

Therefore, these results represent the first genome-wide analysis of DNA replication in *X. laevis*, and demonstrate that an advantage of using molecular combing to analyze DNA replication is the ability to obtain a statistically significant number of measurements using a relatively small sample of DNA. This permits a statistically significant quantitative analysis of DNA replication. We have demonstrated the reliability of the approach using the *Xenopus laevis* cell-free system as a model. However, it is understood that this approach can be used to analyze any kind of genomic DNA, including human DNA. Therefore, this approach is useful for a wide range of studies involving the control of DNA replication, genome stability and the dynamic, and structural relationships regulating DNA replication and gene transcription during development.

The references cited herein are listed on the following pages and are expressly incorporated by reference.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

BIBLIOGRAPHY

1. Litmanovitch, T.; Altaras, M. M.; Dotan, A.; Avivi, L.; Cytogenetics & Cell Genetics. 81(1):26–35, 1998.
2. Schimke, R. T.; Sherwood, S. W.; Hill, A. B.; Johnston, R. N.; Proceedings of the National Academy of Sciences of the United States of America. 83(7):2157–61,1986.
3. Auerbach, A. D.; Verlander P C. Current Opinion in Pediatrics. 9(6):600–16, 1997.
4. Amiel, A.; Litmanovitch, T.; Lishner, M.; Mor, A.; Gaber, E.; Tangi, I.; Fejgin, M.; Avivi, L.; Genes, Chromosomes & Cancer. 22(3):225–31, 1998.
5. Amiel, A.; Litmanovich, T.; Gaber, E.; Lishner, M.; Avivi, L.; Fejgin, M. D.; Human Genetics. 101(2):219–22, 1997.
6. Elledge, S. J.; Science. 274(5293):1664–72, 1996 Stillman, B.; Cell cycle control of DNA replication. Science. 274(5293):1659–64, 1996.
7. Morrow, D. M.; Connelly, C.; Hieter, P.; Genetics. 147(2):371–82, 1997.
8. Hand, R.; Eucaryotic DNA: organization of the genome for replication. Cell. 15(2):317–25, 1978. Hyrien, O.; Maric, C.; Mechali, M.; Transition in specification of embryonic metazoan DNA replication origins. Science. 270(5238):994–7, 1995
9. Walter, J.; Newport, J. W.; Science. 2–75(5302):993–5, 1997.
10. Diffley, J. F.; Once and only once upon a time: specifying and regulating origins of DNA replication in eukaryotic cells. Genes & Development. 10(22):2819–30, 1996.
11. DePamphilis, N. L.; Methods. 13(3):211–9, 1997.
12. Bensimon, A.; Simon, A.; Chiffaude, A.; Croquette, V.; Heslot, F.; Bensimon, D.; Science. 265(5181):2096–8, 1994.
13. Michalet, X.; Ekong, R.; Fougerousse, F.; Rousseaux, S.; Schurra, C.; Hornigold, N.; van Slegtenhorst, M.; Wolfe, J.; Povey, S.; Beckmann, J. S.; Bensimon, A.; Science. 277(5331):1518–23,1997.
14. Herrick, J.; Bensimon, A.; (1999) Chromosome -research, in press.
15. Blow, J. J.; Laskey, R. A.; Cell 47(4):577–87, 1986.
16. Newport, J. W.; Kirschner, M. W.; Cell 30, 675 1982.
17. Harland R. M., Laskey R. A.; (1980) Regulated replication of DNA microinjected into eggs of *Xenopus laevis*. Cell. 21 (3):761–71
18. Mechali, M.; Kearsey, S.; (1984) Lack of specific sequence requirement for DNA replication in Xenopus eggs compared with high sequence specificity in yeast. *Cell.* 38(1):55–64.
19. Laskey, R. A.; Journal of Embryology & Experimental Morphology. 89 Suppl:285–96, 1985.
20. Coverley, D.; Laskey, R. A.; Regulation of eukaryotic DNA replication. Annual *Review of Biochemistr_y*. 63:745–76, 1994.
21. Hyrien, O; Maric, C.; Lucas, I; Role of nuclear architecture in the initiation of eukaryotic DNA replication. [Review] [79 refs] [Journal, Article. Review. Review, Tutorial] Biochimie: 79(9–10);541–8, 1997.
22. Mahbubam, H. M.; Paul, T.; Elder, J. K.; Blow, J. J.; Nucleic Acids Research. 20(7):1457–62, 1992).
23. Blow, J. J.; Watson, J. V.; Nuclei act as independent and integrated units of replication in a Xenopus cell-free DNA replication system. EMBO Journal. 6(7):1997–2002; 1987.
24. Blumenthal, A. B.; Kriegstein, H. J.; Hogness, D. S.; Cold Spring Harbor Symposia on Quantitative Biology. 38:205–23, 1974.
25. Jackson, D. A.; Pombo, A.; Journal of Cell Biology. 140(6):1285–95, 1998.
26. The resolution of molecular combing is 1 to 4 kb. A doubly labeled control sample revealed a background of 50% (false positives) for eye sizes between 0.5 and 3 kb.
27. Hyrien, O.; Mechali, M.; (1993) Chromosomal replication initiates and terminates at random sequences but at regular intervals in the ribosomal DNA of Xenopus early embryos. *EMBO Journal*. 12(12): 4511–20.
28. Weksberg, R.; Squire, J. A.; Molecular biology of Beckwith-Wiedemann syndrome. (Review) [65 refs] [Journal Article. Review. Review, Tutorial Medical & Pediatric Oncology. 2 7 (5): 4 62–9, 19 9 6.

What is claimed is:

1. A method for detecting an origin of replication in a DNA molecule, comprising:
    a) incubating DNA undergoing replication in the presence of labeled nucleotides, wherein the labeled nucleotides are incorporated into the replicating DNA;
    b) aligning the DNA from step a) on a substrate; and
    c) detecting the labeled nucleotides that were incorporated into the DNA during replication, wherein the labeled nucleotides are located in a region that corresponds to the origin of replication.

2. The method according to claim 1, wherein the labeled nucleotides are detected with a labeled probe that binds to the labeled nucleotides.

3. The method according to claim 2, wherein the labeled probe is an antibody conjugated to a label.

4. The method according to claim 3, wherein the label is fluorescent.

5. The method according to claim 2, wherein the DNA is incubated with the labeled probe before the DNA is aligned on the substrate.

6. The method according to claim 1, wherein the DNA is incubated with a labeled probe after the DNA is aligned on the substrate.

7. The method according to claim 5 or 6, further comprising washing the DNA following incubation with the labeled probe to eliminate non specific reagents.

8. The method according to claim 1, further comprising washing the DNA before aligning it on the substrate.

9. The method according to claim 1, wherein the DNA is genomic DNA.

10. The method according to claim 1, wherein the substrate is glass.

11. A method of measuring the rate of DNA replication, comprising:
    a) adding a first labeled nucleotide to a reaction mixture, wherein the reaction mixture comprises DNA undergoing replication, and wherein the first labeled nucleotide is incorporated into the replicating DNA;

b) adding a second labeled nucleotide to the reaction mixture at different time intervals following the addition of the first labeled nucleotide, wherein the second labeled nucleotide is incorporated into the replicating DNA;

c) aligning the DNA from the reaction mixture on a substrate;

d) detecting the first and second labeled nucleotides, which were incorporated into the DNA during replication; and e) measuring the distribution of the first and second labeled nucleotides in the aligned DNA to determine the rate of DNA replication.

12. The method according to claim 11, wherein the first labeled nucleotide is detected with a first labeled probe that binds to the first labeled nucleotide, and the second labeled nucleotide is detected with a second labeled probe that binds to the second labeled nucleotide.

13. The method according to claim 12, wherein the first labeled probe is an antibody conjugated to a first label, and the second labeled probe is an antibody conjugated to a second label, wherein the first and second label are different.

14. The method according to claim 13, wherein the first and second label are fluorescent.

15. The method according to claim 12, wherein the DNA is incubated with the first and second labeled probe before the DNA is aligned on the substrate.

16. The method according to claim 12, wherein the DNA is incubated with the first and second labeled probe after the DNA is aligned on the substrate.

17. The method according to claim 15 or 16, further comprising washing the DNA following incubation with the first and second probe to eliminate non specific reagents.

18. The method according to claim 11, further comprising washing the DNA before aligning it on the substrate.

19. The method according to claim 11, wherein the DNA is genomic DNA.

20. The method according to claim 11, wherein the substrate is glass.

21. The method according to claim 20, wherein the first labeled nucleotide is biotin-dUTP and the second labeled nucleotide is digoxigenin-dUTP.

22. A method of mapping an origin of replication in a DNA molecule, comprising:

a) incubating DNA undergoing replication in the presence of labeled nucleotides, which are incorporated into the replicating DNA;

b) aligning the DNA from step a) on a substrate;

c) hybridizing the aligned DNA with a nucleotide probe;

d) detecting the labeled nucleotides and the nucleotide probe; and e) measuring the distances between the labeled nucleotides that were incorporated into the DNA during replication and the nucleotide probe to determine the location of the origin of replication with respect to the nucleotide probe.

23. The method according to claim 22, wherein the labeled nucleotides are detected with an antibody conjugated to a label.

24. The method according to claim 23, wherein the label is fluorescent.

25. The method according to claim 23, further comprising washing the DNA following incubation with the antibody to eliminate non specific reagents.

26. The method according to claim 23, further comprising washing the DNA before aligning it on the substrate.

27. The method according to claim 23, wherein the DNA is genomic DNA.

28. The method according to claim 23, wherein the substrate is glass.

* * * * *